United States Patent
Haley et al.

(10) Patent No.: US 9,782,368 B2
(45) Date of Patent: Oct. 10, 2017

(54) USE OF N,N-BIS-2-MERCAPTOETHYL ISOPHTHALAMIDE

(71) Applicant: EMERAMED LIMITED, Dublin (IE)

(72) Inventors: Boyd Eugene Haley, Nicholasville, KY (US); Ragnar Axel Theodor Klingberg, Stockholm (SE)

(73) Assignee: Emeramed Limited, Dublin (IE)

( * ) Notice: Subject to any disclaimer, the term of this patent is extended or adjusted under 35 U.S.C. 154(b) by 0 days.

(21) Appl. No.: 15/129,654

(22) PCT Filed: Mar. 31, 2015

(86) PCT No.: PCT/GB2015/050999
§ 371 (c)(1),
(2) Date: Sep. 27, 2016

(87) PCT Pub. No.: WO2015/150793
PCT Pub. Date: Oct. 8, 2015

(65) Prior Publication Data
US 2017/0157072 A1      Jun. 8, 2017

(30) Foreign Application Priority Data
Apr. 4, 2014    (GB) .................................. 1406115.4

(51) Int. Cl.
*A61K 31/166*   (2006.01)
*A61K 45/06*    (2006.01)

(52) U.S. Cl.
CPC ........... *A61K 31/166* (2013.01); *A61K 45/06* (2013.01)

(58) Field of Classification Search
CPC .................................................. A61K 31/166
USPC ......................................................... 514/617
See application file for complete search history.

(56) References Cited

U.S. PATENT DOCUMENTS

| 6,586,600 B2 | 7/2003 | Atwood et al. | |
| 8,426,368 B2 | 4/2013 | Haley et al. | |
| 2010/0227812 A1* | 9/2010 | Haley | A61K 31/16 |
| | | | 514/21.91 |
| 2011/0237525 A1 | 9/2011 | Haley et al. | |
| 2011/0237776 A1 | 9/2011 | Haley et al. | |

FOREIGN PATENT DOCUMENTS

| WO | 2011/038385 A2 | 3/2011 |
| WO | 2012/121798 A2 | 9/2012 |

OTHER PUBLICATIONS

Patel et al., "Thio-redox Protect Against Lung Vascular Endothelial Cytoskeletal Alterations Caused by Pulmonary Fibrosis Inducer, Bleomycin: Comparison Between Classical Thiol-protectant, N-acetyl-l-cysteine, and Novel Thiol Antioxidant, N,N'-bis-2-mercaptoethyl isophthalamide," Toxicology Mechanisms and Methods 22 (5):383-396 (2012).

(Continued)

*Primary Examiner* — Kathrien Cruz
*Assistant Examiner* — Janet L Coppins
(74) *Attorney, Agent, or Firm* — LeClairRyan, a Professional Corporation

(57) ABSTRACT

According to the invention there is provided N,N-bis-2-mercaptoethyl isophthalamide, or a pharmaceutically acceptable salt or derivative thereof, for use in regenerating ascorbate systemically and thus in the therapeutic treatment of chronic obstructive pulmonary disease.

11 Claims, 2 Drawing Sheets

(56) References Cited

OTHER PUBLICATIONS

Figure 1:
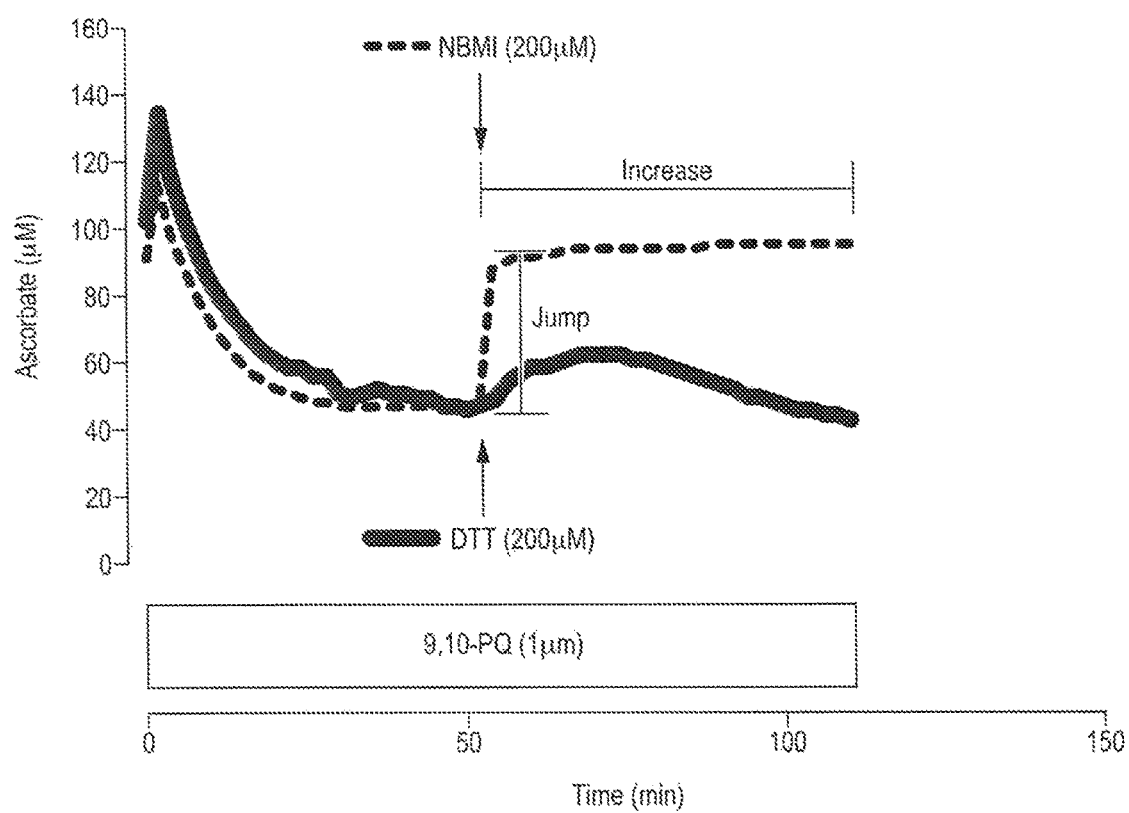

Rahman, Irfan, "Antioxidant Therapeutic Advances in COPD," Therapeutic Advances in Respiratory Disease 2 (6):351-374 (2008).
PCT International Search Report and Written Opinion corresponding to PCT/GB2015/050999, mailed Jul. 14, 2015.
Great Britain Search Report corresponding to GB1406115.4, mailed Jan. 28, 2015.
PCT International Preliminary Report on Patentability corresponding to PCT/GB2015/050999, mailed Nov. 4, 2015.
Moeller et al., "The Bleomycin Animal Model: A Useful Tool to Investigate Treatment Options for Idiopathic Pulmonary Fibrosis", The International Journal of Biochemistry and Cell Biology, 40:362-382 (2008).
Corti et al., "Cellular Pathways for Transport and Efflux of Ascorbate and Dehydroascorbate", Archives of Biochemistry and Biophysics, 500:107-115 (2010).
Saaranen et al., "The Role of Dehydroascorbate in Disulfide Bond Formation", Antioxidants & Redox Signaling, 12(1):15-25 (2010).
Nardi et al., "Protein-Disulfide Isomerase- and Protein Thio-Dependent Dehydroascorbate Reduction and Ascorbate Accumulation in the Lumen of the Endoplasmic Reticulum", Journal of Biological Chemistry, 276(12):8825-8828 (2001).
Winkler et al., "The Redox Couple Between Glutathione and Ascorbic Acid: A Chemical and Physiological Perspective", Free Radical Biology & Medicine, 17(4):333-349 (1994).
Rossman et al., "Ascorbate Infusion Increases Skeletal Muscle Fatigue Resistance in Patients with Chronic Obstructive Pulmonary Disease", American Journal Physiol Regul Integr Comp Physiol, 305:R1163-R1170 (2013).
Rubini, "Interleukin-6 and Lung Inflammation: Evidence for a Causative Role in Inducing Respiratory System Resistance Increments", Inflammation & Allergy Drug Targets, 12:315-321 (2013).
Thorleifsson et al., "Chronic Airflow Obstruction and Markers of Systemic Inflammation: Results from the BOLD Study in Iceland", Respiratory Medicine, 103:1548-1553 (2009).
Tang et al., "The Role of the Serum IL-33/sST2 Axis and Inflammatory Cytokines in Chronic Obstructive Pulmonary Disease", Journal of Interferon & Cytokine Research, 34(3):162-168 (2014).
Dadvand et al., "Air Pollution and Biomarkers of Systemic Inflammation and Tissue Repair in COPD Patients", J. Eur. Respir., 44:603-613 (2014).
Clarke et al.,"Amelioration of Acute Mercury Toxicity by a Novel, Non-Toxic Lipid Soluble Chelator N,N'bis-(2-mercaptoethyl)isophthalamide: Effect on Animal Survival, Health, Mercury Excretion, and Organ Accumulation", Toxicological & Environmental Chemistry, pp. 1-25 (2012).
Meister, "Glutathione-Ascorbic Acid Antioxidant System in Animals", Journal of Biological Chemistry, 269 (13):9397-9400 (1994).
Global Initiative for COPD, "Global Strategy for the Diagnosis, Management, and Prevention of Chronic Obstructive Pulmonary Disease" (2013).
May et al., "Ascorbate Recycling in Human Erythrocytes: Role of GSH in Reducing Dehydroascorbate", Free Radical Biology & Medicine, 20(4):543-551 (1996).
Zheng et al., "Twice Daily N-Acetylcysteine 600 mg for Exacerbations of Chronic Obstructive Pulmonary Disease (PANTHEON): A Randomised, Double-Blind Placebo-Controlled Trial", The Lancet Respiratory Medicine, 2(3):187-194 (2014) (Abstract only).
https://www.blf.org.uk/Page/IPF-Patient-differential-diagnosis-of-COPD (printed Sep. 24, 2015).
Declaration of Ragnar Klingberg under 37 C.F.R. 1.98 (with Exhibits 1 and 2) (executed Mar. 2, 2017).

* cited by examiner

USE OF N,N-BIS-2-MERCAPTOETHYL ISOPHTHALAMIDE

This application is a national stage application under 35 U.S.C. §371 of PCT Application No. PCT/GB2015/050999, filed 31 Mar. 2015, which claims the priority benefit of Great Britain Patent Application No. 1406115.4, filed 4 Apr. 2014.

FIELD OF THE INVENTION

This invention relates to a new use of a known heavy metal-chelating compound.

BACKGROUND AND PRIOR ART

Chronic obstructive pulmonary disease (COPD) is an obstructive lung disease that is characterized by chronically poor airflow, shortness of breath, cough, and sputum production.

Worldwide COPD is thought to affect nearly 600,000,000 individuals. The overwhelming majority of patients with COPD are smokers or ex-smokers.

COPD is known to have many possible causes, with tobacco smoking being the most common. Other causes include air pollution, particularly from the burning of fuel (e.g. wood smoke). There is also believed to be a genetic component to the disorder.

It is understood that COPD is caused by long-term exposure to these irritants, giving rise to an inflammatory response in the lungs. This results in constriction of bronchi and breakdown of lung tissue (emphysema).

Although COPD is thought to be a largely preventable disease (for example by reducing exposure to the pathogens that cause it), it is still the world's third commonest cause of death.

Treatment of sufferers presents a significant challenge. Current frontline treatments include inhaled bronchodilators and corticosteroids. However, airflow reduction in COPD sufferers generally does not improve significantly with the administration of currently-employed medications, meaning that, often, more drastic measures including oxygen therapy and even lung transplantation are employed. Worsening of symptoms often requires hospitalization.

Due to the lack of effective treatments, the economic burden of COPD is enormous, being an estimated at $2.1 trillion in 2010. The socio-economic cost of COPD is likely to increase as longevity in developed and the developing world increases. In the EU, the direct cost of treatment of the 2 million worst affected patients is around €30Bn per year (€15.000 per patient per year). Direct costs of treatments of the other 20 million affected is around €10Bn (€500 per patient per year). The total cost is thus around €40Bn, not including additional indirect costs due to lost productivity. Co-morbidities are very common in COPD, which further inflates the cost of treatment.

Thus, there is a huge, clinically-unmet need for new and/or better treatments of COPD. There is also a clear need for improved therapies able to target key pathological processes with the potential to modify the progression of the disease, reducing the number of patients progressing to the more severe stages of the disease.

N,N-bis-2-mercaptoethyl isophthalamide (NBMI) was first disclosed in US patent number U.S. Pat. No. 6,586,600 B2. Its use as a dietary supplement, and in the relief of oxidative stress is disclosed in US patent application 2010/0227812. NBMI is known to be a powerful chelator of heavy metals, including mercury, cadmium and lead. See also Patel et al, *Toxicology Mechanisms and Methods,* 22, 383 (2012).

Analogues of NBMI have been disclosed in inter alia U.S. Pat. No. 8,426,368 B2 and international patent applications WO 2011/038385 and WO 2012/121798.

However, none of the aforementioned documents disclose the potential use of NBMI or related compounds in the potential treatment of COPD.

It is known generally that increased oxidative stress occurs within the lungs and systemically in COPD patients, both as a result of the oxidative burden from cigarette smoke itself and from the increased release of reactive oxygen species (ROS) from inflammatory cells activated as a result.

Intracellular eukaryotic cells possess enzyme systems that regenerate ascorbate from its oxidized product, dehydroascorbate (DHA), so preventing its irreversible oxidation to downstream products that lack antioxidant function (see e.g. Corti et al, *Arch. Biochem. Biophys.,* 500, 107 (2010)). This mechanism is therefore essential for maintain cellular ascorbate concentrations and can occur either enzymatically through the action of dehydroascorbate reductases such as glutaredoxin (see Saaranen et al, *Antioxid. Redox Signal.,* 12, 15 (2010)) and protein disulfide isomerise (Nardai et al, *J. Biol. Chem.,* 276, 8825 (2001)), as well as non-enzymatically through its reduction by GSH (Winkler et al, *Free Radic. Biol. Med.,* 17, 333 (1994)).

A recent study has shown that ascorbate infusion increases skeletal muscle fatigue resistance in patients with COPD (see e.g. Rossman et al, *Am. J. Physiol. Regul. Integr. Comp. Physiol.,* 305, (2013)).

We have found, not only that NBMI is capable of inhibiting release of key anti-inflammatory markers, such interleukin-6 (IL-6), interleukin-8 (IL-8) and tumor necrosis factor-alpha (TNF-α) that are known to be expressed in COPD patients (see, for example, Rubini, et al, *Inflamm. Allergy Drug Targets,* 12, 315 (2013), Thorleifsson et al, *Respir. Med.,* 103, 1548 (2009) and Tang, *J. Interferon Cytokine Res.,* 34, 162 (2014) and Dadvand et al, *Eur. Respir. J.,* (2014 Feb. 20), but also, very surprisingly, that NBMI is capable of re-generating ascorbate within the airway lining fluid. Further, it has been found that NBMI may exert this action by functioning as an electron donor for ascorbate recycling. We have also found, surprisingly, that NBMI may be administered to patients to treat COPD therapeutically by ameliorating symptoms and modifying/abrogating the progression of the disease, without giving rise to significant adverse side effects.

DISCLOSURE OF THE INVENTION

According to a first aspect of the invention there is provided NBMI, or a pharmaceutically-acceptable salt thereof or derivative thereof, for use in a method of treating COPD. Such a method comprises administering a pharmaceutically-effective amount of NBMI to a patient in need of such treatment.

The term "COPD" will be understood to include those conditions referred to in the literature variously as "chronic obstructive lung disease (COLD) or chronic obstructive airway disease (COAD)", characterised for example by chronically poor airflow, shortness of breath, cough, and sputum production.

For the avoidance of doubt, in the context of the present invention, the terms "treatment", "therapy" and "therapy method" include the therapeutic, or palliative, treatment of patients in need of, COPD, or other relevant conditions mentioned herein. "Patients" include human patients.

Pharmaceutically-acceptable salts of NBMI that may be mentioned include alkaline earth, and more particularly alkali, metal salts, such as lithium, sodium, potassium, rubidium, caesium and francium salts.

Such salts may be formed by conventional means, for example by reaction of NBMI with one or more equivalents of an appropriate base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of an active ingredient in the form of a salt with another counter-ion, for example using a suitable ion exchange resin.

Pharmaceutically-acceptable derivatives of NBMI include glutathione, cysteine, alphadihydrolipoic acid, cystamine, thiolphosphate, 5'-thioladenosine, L-homocysteine, co-enzyme A, 2-mercaptoethanol, dithiothreitol, iodoacetate, bromoacetate, fluoroacetate or chloroacetate derivatives. Such derivatives may be prepared as described in, for example, US patent application 2011/0237776.

NBMI, pharmaceutically-acceptable salts thereof, and pharmaceutically-acceptable derivatives thereof are collectively referred to together hereinafter simply as "NBMI".

According to a further aspect of the invention there is provided a method of treating COPD in a patient by administering NBMI at a sufficient, pharmaceutically-effective dose capable of regenerating ascorbate (e.g. systemically) in that patient.

The skilled person will be well aware that "ascorbate" may also be referred to variously in the literature as ascorbic acid, L-ascorbic acid and/or vitamin C.

COPD is known to be linked to respiratory morbidity and mortality, the risk of which may, in accordance with the invention, be reduced with NBMI.

According to a further aspect of the invention there is provided a method of reducing the risk of (i.e. preventing) respiratory morbidity and mortality in a patient, which method comprise administering NBMI to such a patient exhibiting symptoms of COPD.

The term "morbidity" will be understood by the skilled person to include any at least partially debilitating diseased state, disability or illness, and/or poor health generally. "Respiratory" morbidity therefore includes such states exhibited as a consequence of e.g. COPD.

NBMI has been found to be of use in the relief of symptoms of COPD, including fatigue (e.g. skeletal muscle fatigue), shortness of breath, cough and sputum production.

According to a further aspect of the invention there is provided a method of relieving one or more symptom of COPD in a patient suffering from COPD, which method comprise administering NBMI to such a patient.

Although not limited as such, uses and methods of treatment according to the invention include that may be mentioned include those in which the patient is a smoker or is an ex-smoker.

In the uses and methods described herein, NBMI is preferably administered locally or systemically, for example orally, intravenously or intraarterially (including by intravascular or other perivascular devices/dosage forms (e.g. stents)), intramuscularly, cutaneously, subcutaneously, transmucosally (e.g. sublingually or buccally), rectally, transdermally, nasally, pulmonarily (e.g. by inhalation, tracheally or bronchially), topically, or by any other parenteral route, in the form of a pharmaceutical preparation comprising the compound in a pharmaceutically acceptable dosage form. Preferred modes of delivery include oral (particularly), intravenous, cutaneous or subcutaneous, nasal, intramuscular, or intraperitoneal delivery.

NBMI will generally be administered in the form of one or more pharmaceutical formulations in admixture with a pharmaceutically acceptable adjuvant, diluent or carrier, which may be selected with due regard to the intended route of administration and standard pharmaceutical practice. Such pharmaceutically acceptable carriers may be chemically inert to the active compounds and may have no detrimental side effects or toxicity under the conditions of use. Such pharmaceutically acceptable carriers may also impart an immediate, or a modified, release of NBMI.

Suitable pharmaceutical formulations may be commercially available or otherwise are described in the literature, for example, Remington *The Science and Practice of Pharmacy*, 19th ed., Mack Printing Company, Easton, Pa. (1995) and *Martindale—The Complete Drug Reference* (35th Edition) and the documents referred to therein, the relevant disclosures in all of which documents are hereby incorporated by reference. Otherwise, the preparation of suitable formulations may be achieved non-inventively by the skilled person using routine techniques. Suitable pharmaceutical formulations for use with NBMI are also described in US patent application 2010/0227812.

The amount of NBMI in the formulation will depend on the severity of the condition, and on the patient, to be treated, as well as the compound(s) which is/are employed, but may be determined non-inventively by the skilled person.

Depending on the patient to be treated, as well as the route of administration, NBMI may be administered at varying therapeutically effective doses to a patient in need thereof.

However, the dose administered to a human, in the context of the present invention should be sufficient to effect a therapeutic response over a reasonable timeframe (as described hereinbefore). One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the age, condition, body weight, sex and response of the patient to be treated, and the stage/severity of the disease, as well as genetic differences between patients.

Administration of NBMI may be continuous or intermittent (e.g. by bolus injection). The dosage may also be determined by the timing and frequency of administration.

Suitable doses of NBMI are therefore in the range of about 0.5 and about 100.0 mg, including between about 1 and about 60 mg, for example between about 1.5 and about 40 mg of the compound per kilogram of the patient's total body weight per day.

In any event, the medical practitioner, or other skilled person, will be able to determine routinely the actual dosage, which will be most suitable for an individual patient. The above-mentioned dosages are exemplary of the average case; there can, of course, be individual instances where higher or lower dosage ranges are merited, and such are within the scope of this invention.

In the uses and methods described herein, NBMI may also be combined with one or more active ingredients that are potentially useful, or have been indicated for use, in the treatment of COPD. Such patients may thus also (and/or already) be receiving therapy based upon administration of one or more of such active ingredients, by which we mean receiving a prescribed dose of one or more of those active ingredients mentioned herein, prior to, in addition to, and/or following, treatment with NBMI.

Such active ingredients include short-acting bronchodilators (such as salbutamol/albuterol, levosalbutamol/levalbuterol, pirbuterol, epinephrine, ephedrine and terbutaline), long-acting bronchodilators (such as salmeterol, clenbuterol, formoterol, bambuterol and indacaterol), anticholinergics (such as tiotropium and ipratropium bromide), corticosteriods (such as flunisolide, fluticasone propionate, triamcinolone acetonide, beclomethasone dipropionate and budesonide), and other drugs used in the treatment of COPD, including long-term antibiotics (e.g. macrolides, such as erythromycin), mucolytics and oxygen.

NMBI may also be co-administered with antioxidants or chelators, including vitamin-E, vitamin-D, cysteine, cystine, glutathione, lipoic acid glutathione (GSH), dihydrolipoic acid (DLPA), lipoic acid (LPA), N-acetylcysteine (NAC), dimercaptopropane sulfonate (DMPS), dimercaptosuccinic acid (DMSA), ethylenediaminetetraacetic acid (EDTA), and mixtures thereof.

Pharmaceutically-acceptable salts of other active ingredients useful in the treatment COPD that may be mentioned include acid addition salts and base addition salts. Such salts may be formed by conventional means.

Suitable doses of other active ingredients include those that are useful in the treatment of COPD are known to those skilled in the art and include those listed for the drugs in question to in the medical literature, such as *Martindale—The Complete Drug Reference* (35th Edition) and the documents referred to therein, the relevant disclosures in all of which documents are hereby incorporated by reference.

Wherever the word "about" is employed herein, for example in the context of amounts (e.g. doses of active ingredients), it will be appreciated that such variables are approximate and as such may vary by ±10%, for example ±5% and preferably ±2% (e.g. ±1%) from the numbers specified herein.

The uses/methods described herein may have the advantage that, in the treatment of COPD, they may be more convenient for the physician and/or patient than, be more efficacious than, be less toxic than, have a broader range of activity than, be more potent than, produce fewer side effects than, or that it may have other useful pharmacological properties over, similar methods (treatments) known in the prior art for use in such therapy.

The invention is illustrated, but in no way limited, by the following example, in which:

FIG. 1 illustrates, in an ascorbate oxidation model, oxidation of ascorbate to DHA by 9,10-phenanthrenequinone (9,10-PQ), followed by re-cycling of DHA by NMBI and dithiothreitol (DTT).

Figure 2:
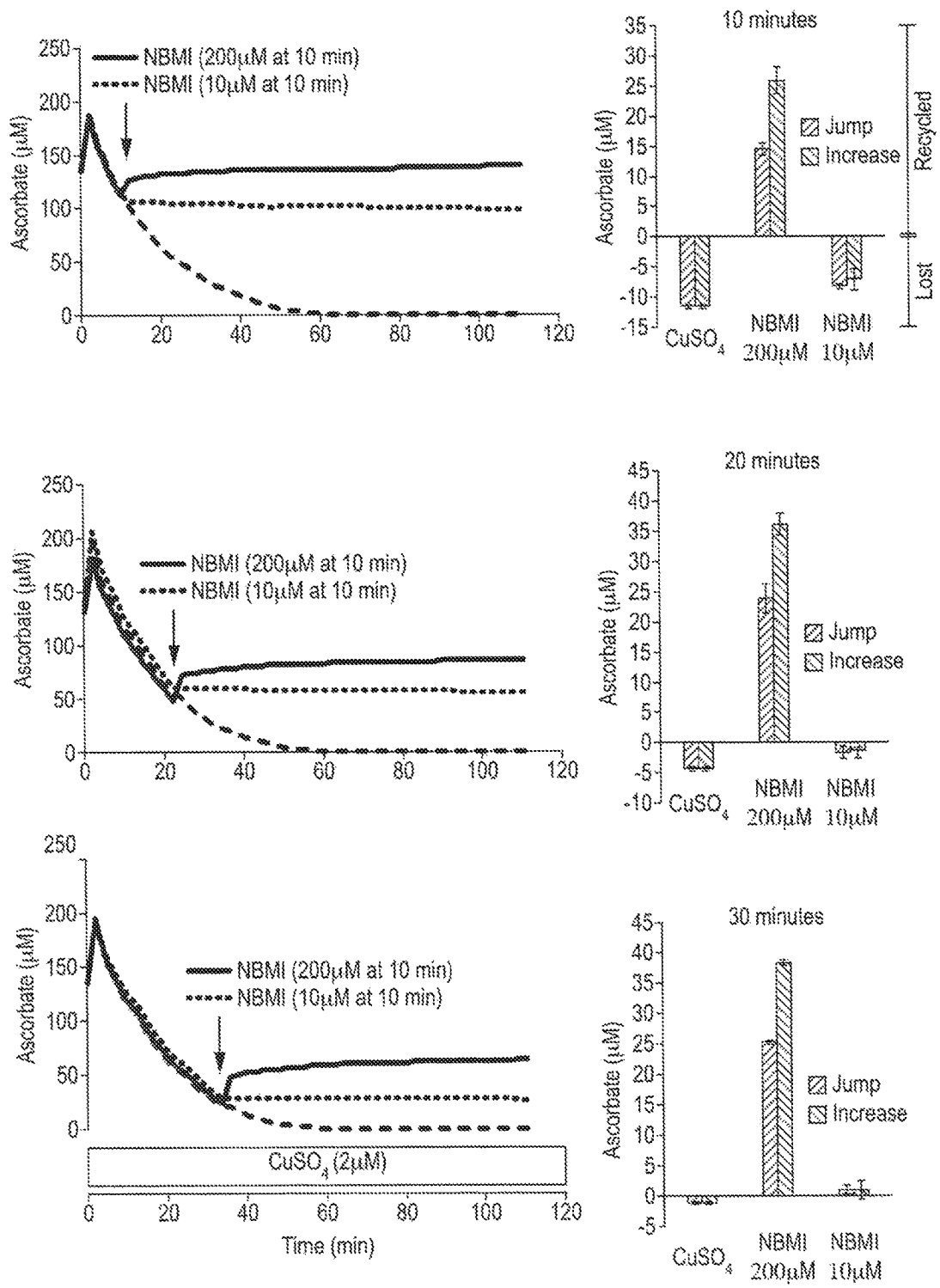

FIG. 2 illustrates, in an ascorbate oxidation model, oxidation of ascorbate to DHA by $CuSO_4$, followed by NBMI and DTT recycling of DHA with addition at 10, 20 and 30 minutes, with the ascorbate oxidation and recycling kinetics shown in the left hand panel, and the corresponding immediate jump and sustained increase in ascorbate concentrations after the addition of NBMI and DTT shown in the right hand panel.

EXAMPLE 1

Inhibition of IL-6 and IL-8 Using NBMI

Secretion of the pro-inflammatory cytokines interleukin (IL)-6, IL-8 (as well as GM-CSF and MCP-1) into cell media in response to particle exposure was measured in A549 and BEAS-2B cells using the following method.

Lung epithelial cells were seeded at $5 \times 10^4$ in 24-well plates. After pre-incubation with NBMI, the anti-oxidant compound, N-acetyl-L-cysteine (NAC), which was used as a positive control, or vehicle, for 3 hours the medium was removed.

Fresh media containing various particles (as below) in different concentrations was in a total volume of 0.5 ml for an additional 24 hours. The supernatants were then separated from the cells by centrifugation.

IL-8, IL-6, GM-CSF and MCP-1 were measured in the cell free fluid using the DuoSet ELISA Development kit (R&D Systems, Abingdon, UK) according to manufacturer's protocol.

Exposure to medium only served as negative control. Each experiment was performed twice with 4 replicates.

In general, both titanium dioxide type P25 and urban dust (reference SRM 1649 b) induced production of pro-inflammatory cytokines in the lung epithelial cell lines A549 and BEAS-2B.

The effect of pre-incubation with 50 μM NBMI on particle-induced cytokine formation was tested at various concentrations of relevant particles.

The study demonstrated that NBMI can reduce the particle-induced secretion of pro-inflammatory cytokines in both cell lines, although the reduction was only in some cases reduced to background levels.

The highest concentrations of IL-8 and IL-6 were achieved in supernatants of A549 cells exposed to $TiO_2$ P25 at 75 μg/cm². At this dose, 50 μM NBMI reduced the secretion of IL-8 with 29% and IL-6 with 38%.

At 100 μg/cm² of Urban Dust in A549 cells, pre-incubation with 50 μM NBMI reduced the secretion of IL-8 with 30%, and IL-6 with 38%.

At 100 μg/cm² of $TiO_2$ P25 in BEAS-2B cells, pre-incubation with 50 μM NBMI reduced the secretion of IL-8 with 49%, and IL-6 with 37%.

At 100 μg/cm² of Urban Dust in BEAS-2B cells, pre-incubation with 50 μM NBMI reduced the secretion of IL-6 with 47%.

Pre-incubation with 5 mM NAC was also effective in reducing the secretion of inflammatory cytokines.

EXAMPLE 2

Regeneration of Ascorbate Using NBMI

NBMI was examined to see if it could function as an electron donor for ascorbate recycling.

The kinetics of ascorbate oxidation, sponsored by both 1 μM 9,10-PQ and 2 μM copper sulphate ($CuSO_4$), was examined using the ascorbate depletion assay (Kelly et al, *Res. Rep. Health Eff. Inst.*, 163, 3 (2011). 9,10-PQ was employed so that the action of NBMI could be examined in isolation of its chelation properties.

All experiments were performed in triplicate in UV 96 well flat-bottomed plates (Greiner bio-one) at a final volume of 200 μL. Exposures were initiated by the addition of 20 μL of a concentrated stock of ascorbate (2 mM) into each well containing 160 μL of Chelex-100 resin treated water (containing 10% DMSO), plus either 10 μL of water, $CuSO_4$ stock solution at 4 mM or 9,10-PQ stock solution at 2 mM, and 10 μL of NMBI (4 mM and 200 μL).

All solutions were prepared in Chelex-100 resin treated water (containing 10% DMSO). This yielded final concentrations in the wells of 200 μL ascorbate, 2 μM $CuSO_4$, or 1 μM 9,10-PQ and between 10 and 200 μM of NBMI.

Immediately prior to the addition of the ascorbate to each assay well, the plate was pre-incubated for 10 minutes at 37° C. in a plate reader (Spectra Max 190). During the exposure, the plate was maintained at this temperature. After addition of ascorbate, the concentration remaining in each well was monitored every 2 minutes for a period of two hours by measuring the absorbance at 265 nm. The ascorbate concentration was determined with reference to a standard curve, with the rate of ascorbate oxidation determined by performing a linear regression through the initial part of a concentration verses time plot using Microcal Software Limited's OriginLab (version 5.0). This was performed for each of the triplicates and the rate of ascorbate depletion was finally expressed as mean mol s $1 \times 10^{-9}$ depletion of ascorbate±standard deviation.

For the experiments in which the impact of adding NBMI to the ascorbate was measured, $CuSO_4$ and 9,10-PQ depletion assays were examined later in the time course. The plates were ran with 190 µL only for the first 55-60 minutes, after which they were removed from the plate reader and 10 µL of either the NMBI or the known reducing agent, DTT stock solution, or water was added to each well. The plate was then returned to the plate reader and the absorbance at 265 nm monitored for a further 60 minutes.

The immediate increase in the measured ascorbate concentrations was determined and is referred to as the 'jump', as a measure of immediate recycling capacity. The sustained 'increase' over the remaining 60 minutes of the incubation was also determined. The difference between the two reflects the capacity of the added compounds to subsequently inhibit the rate of $CuSO_4$- or 9,10-PQ-sponsored ascorbate oxidation.

FIG. 1 shows the kinetics of ascorbate oxidation sponsored by incubation with 9,10-PQ over the first 60 minutes of the experiment. At this time, NMBI (200 µM) was added and was shown to result in an immediate rebound increase in ascorbate of 42.8 µM. Thereafter, the rate of ascorbate oxidation was reduced relative to the first 60 minute period.

This rebound increase in ascorbate, which indicated the recycling of DHA back to ascorbate, was surprising, and was significantly greater when compared to that achieved using (DTT, 200 µM), which achieved a lower immediate recovery of ascorbate, 5.1 µM, which was also not sustained.

FIG. 2 shows the capacity of NMBI to recycle DHA in the $CuSO_4$ ascorbate model at 10, 20 and 30 minutes into the incubation. Focusing on these earlier time points, the rebound increase in ascorbate following NMBI addition was most marked at the higher of the two tested concentrations, with the subsequent rate of oxidation quenched, possibly due to the chelation properties of the compound.

These experiments were repeated with the addition of NMBI and DTT (both at 200 µM) at 60 minutes. This revealed an immediate 'jump' in ascorbate concentration of 7.93±6.58 µM with DTT compared with a 24.98±5.54 µM increase with NBMI. Over the remaining 60 minutes of the incubation, the sustained 'increase' in ascorbate was 10.79±2.45 µM versus 25.45±2.45 µM for DTT and NBMI respectively.

These results indicate a hitherto unknown and surprising property of NBMI, suggesting that it can recycle DHA back to ascorbate.

EXAMPLE 3

Treatment of Patient with COPD

A retired woman residing in the USA, who had been medically diagnosed with COPD several years earlier, regularly experienced coughing fits two to four times in any 24 hour period, beginning at any hour of the day or night and lasting from about 40 to 75 minutes.

As a consequence of these coughing fits, the patient's breathing was shallow, her throat irritated, her voice was raspy, her energy levels very low and her quality of life very poor.

Treatment three times daily (at meal times) of 100 mg NBMI doses in a capsule for a period of eight days resulted in a marked improvement in symptoms. By the eighth day of treatment, the patient was experiencing no coughing fits and significantly improved breathing.

EXAMPLE 4

In Vivo "Smoking Mouse" Study I

Studies have shown that cigarette smoke can induce an inflammatory lung response in both C57B1/6 and Balb/c mice when exposed to 5-6 cigarettes per day, 5 days per week (see e.g. D'hulst et al, *Eur. Respir. J.*, 26, 204 (2005) and Jung et al, *BMC Complement. Altern. Med.*, 13, 219 (2013)).

A mouse model of cigarette smoke (CS)-induced airway disease was developed, in which four groups of BALB/c mice were exposed to CS (nose-only) using a cigarette smoking machine that produces a combination of side-stream and mainstream smoke from filtered research cigarettes, 7 days a week over 2 weeks.

As part of a 14-day dose-finding study, three groups of mice were administered NMBI subcutaneously (5, 30 or 150 mg/kg) before each exposure to CS. Inflammatory cell counts in bronchoalveolar lavage (BAL), flow cytometry (FACS) analysis and cytokine analysis in BAL were carried out.

Materials and Methods

Female BALB/c mice (Harlem laboratories, Netherlands) were used in this study. They were housed in plastic cages with absorbent bedding material and were maintained on a 12 hour daylight cycle. Food and water were provided ad libitum. Their care and the experimental protocols were approved by the Regional Ethics Committee on Animal Experiments in Umeå. Mice were 12 weeks of age when the cigarette exposure protocol started.

CS-Exposure Protocol

Animals were subjected to inhaled CS (both side-stream and main-stream smoke). The CS exposure was performed in a microprocessor-controlled cigarette smoking machine (TE-10, Teague Enterprises, CA, USA) that produces smoke from research cigarettes (1R5F, University of Kentucky, Lexington, Ky., USA).

Cigarettes are automatically loaded into a wheel, lit, puffed and ejected. Each cigarette was smoked for 10 minutes and the airflow through the machine was set to 12 L/min. Cigarettes were stored at −20° C. until needed. Mice were subjected to 4 cigarettes every 10 minutes×3 (i.e. 12 cigarettes over 30 minutes), once a day, 7 days a week, over two weeks. The smoke was transferred into a smoke tower (EMMS, UK) providing equal and simultaneous exposure to the CS.

Mice were placed into plastic chambers and subjected to CS by "nose-only" inhalation. Control mice were handled every day and breathed room-air, but were not taken out of their cages.

Accordingly, the 5 treatment groups are as follows:
1. Daily exposure to clean air (Placebo Group)
2. Daily exposure to CS (CS-Exposed Placebo Group)
3. Daily exposure to CS; treated with NBMI at a 5 mg/kg dose (NBMI 5 mg/kg Group)
4. Daily exposure to CS; treated with NBMI at a 30 mg/kg dose (NBMI 30 mg/kg Group)
5. Daily exposure to CS; treated with NBMI at a 150 mg/kg dose (NBMI 150 mg/kg Group)

On Day 15, mice were exsanguinated and subjected to bronchoalveolar lavage (BAL). The lungs were lavaged four times via the tracheal tube with a total volume of 1 mL+3×1 mL $Ca^{2+}/Mg^{2+}$ free Hanks' balanced salt solution (HBSS, Sigma-Aldrich, Steinheim, Germany).

The BAL fluid was then immediately centrifuged (10 minutes, 4° C., 1750 rpm). After removing the supernatant until further analysis, the cell pellet was re-suspended and then diluted with 0.5 mL PBS. Leukocytes were counted manually in a hemocytometer so that 20,000 cells could be loaded and centrifuged using a Cytospin® centrifuge (Shandon® cytospin 3 cyto-centrifuge, cell preparation system).

Cytocentrifuged preparations were stained with May-Grünwald-Giemsa reagent and differential cell counts of pulmonary inflammatory cells (macrophages, neutrophils, lymphocytes, and eosinophils) were made using standard morphological criteria and counting 300 cells per cytospin preparation.

Inflammatory mediators in BAL and serum were analyzed for the presence of interleukin (IL)-1α, IL-1β, IL-2, IL-3, IL-4, IL-5, IL-6, IL-9, IL-10, IL-12p40, IL-12p70, IL-13, IL17, Eotaxin, G-CSF, INFγ, GM-CSF, KC, MCP-1, MIP-1α, MIP-1β, RANTES and TNFα. All cytokine analyses were performed simultaneously with a multiplex kit (Bio-Plex™ Pro Mouse Cytokine 23-plex panel) according to the manufacturer's instructions (Bio-Rad) and analyzed on a Bio-Plex™ system (Luminex Bio-Plex™ 200 System, Bio-Rad, Hercules, Calif.).

Leukocytes from BAL were analyzed with flow cytometry using a BD FACSort™ (Becton Dickinson, San Jose, Calif.). Cells from BAL were re-suspended in PBS as described above. Antibody staining was performed in 96-well plates with $2.0 \times 10^5$ cells/sample.

Cells were pre-incubated with FcR blocking Ab (ant-CD16/CD32; clone 2.4G2) to reduce nonspecific binding. The mAbs used to identify subtypes of T cells were: CD3-FITC (clone 17A2), CD4-PE (clone H129.19) and CD8a-PE-Cy5 (clone 53-6.7). Isotype-matched antibodies were used as a negative control. Flow cytometry was performed using a BD FACSort™ (Becton Dickinson, San Jose, Calif.) according to standard procedure and analyzed with BD FACSDiva Software. All antibodies were originated from BD Sciences Pharmingen (San Diego, Calif.). T cells were defined as $CD3^+$.

Results were presented as the mean±standard error of mean (S.E.M). Statistical significance was assessed by parametric methods using a two-way analysis of variance (ANOVA) to determine differences between groups, followed by a Bonferroni post hoc test. When appropriate, a one-way ANOVA or Student's unpaired t-test was used. A statistical result with $p<0.05$ was considered significant.

The statistical analyses were carried out and graphs were prepared with GraphPad Prism (version 6.0 GraphPad software Inc., San Diego, Calif., USA).

Results

All animals were weighed daily from Day 1 until Day 15, 24 hours after last smoke exposure. Mice did not have any significant weight differences on Day 1. On Day 15, the animals in the NBMI 5 mg/kg Group had a lower final weight (19.5±0.3 g) than mice exposed to CS (20.3±0.3 g, p<0.05). All mice exposed to CS regardless of dose of NBMI had lost weight significantly from Day 1 to Day 15.

The total BAL cell count in CS-exposed animals (Day 15) was not significantly higher than control groups (296, 700±43,650 with CS and 284,670±63,200 cells/mL without CS, p>0.05). CS-exposure induced a significant increase of neutrophils in BAL fluid (940±250 with CS and 260±160 cells/mL without CS, p<0.05). On Day 15, the animals in the NBMI 150 mg/kg Group and NBMI 30 mg/kg Group had significantly lower numbers of neutrophils than mice just exposed to CS.

Two weeks of CS-exposure did not significantly increase the levels of inflammatory mediators except for G-CSF in BAL. The NBMI 5 mg/kg Group had lowered MIP-1α levels compared to the CS-Exposed Placebo Group (p<0.05). There were no other significant differences between the inflammatory mediators analysed.

Two weeks of CS-exposure did not significantly increase the levels of inflammatory mediators in serum. The NBMI 150 mg/kg Group had significantly lowered levels of IL-1β, IL-3, IL-6, Eotaxin, MIP-1α and RANTES compared to the CS-Exposed Placebo Group. The NMBI 30 mg/kg Group had increased levels of IL-10 in serum. There were no other significant differences between the inflammatory mediators analyzed.

Two weeks of CS exposure did not significantly increase the levels of either CD4 cells or CD8 cells in BAL fluid. There were no significant differences between any of the groups.

Mice in the NBMI 150 mg/kg Group established wounds in the neck. The two other NBMI Groups showed no signs of ulceration, and neither did either of the Placebo Groups.

EXAMPLE 5

In Vivo "Smoking Mouse" Study II

It was concluded from the results from the study described in Example 4 above that two weeks of cigarette-smoking was possibly not enough time to induce an inflammatory response.

The 14 day dose-finding study was therefore followed by a 90 day study using essentially the same apparatus and protocol described in Example 4 above.

On this occasion, the 5 treatment groups were as follows:
1. Daily exposure to clean air (Placebo Group; Gr. 1)
2. Daily exposure to CS (CS-Exposed Placebo Group; Gr. 2)
3. Daily exposure to CS; treated with NBMI at a 30 mg/kg dose (NBMI 30 mg/kg Group; Gr. 3)
4. Daily exposure to CS; treated with NBMI at a 60 mg/kg dose (NBMI 60 mg/kg Group; Gr. 4)
5. Daily exposure to CS; treated with NBMI at a 150 mg/kg dose (NBMI 150 mg/kg Group; Gr. 5)

On Day 91, animals were weighed and anesthetised with pentobarbital sodium (90 mg/kg body weight, i.p.). Mice were tracheotomised with an 18-gauge cannula and mechanically ventilated in a quasi-sinusoidal fashion with a small animal ventilator (flexiVent™, SCIREQ®) at a frequency of 3 Hz and a tidal volume ($V_T$) of 12 ml/kg body weight. A positive end-expiratory pressure of 3 cm $H_2O$ was applied.

The animal's cardiac output was monitored throughout the respiratory mechanics assessment. Mice were paralysed with pancuronium (0.1 mg/kg body weight, i.p. (local suppliers)) before 4 sigh manoeuvres at 3×$V_T$ were performed at the beginning of the experiment to establish stable baseline respiratory mechanics and to ensure a similar volume history before the experiment.

Dynamic lung mechanics were measured by applying a sinusoidal standardised breath and analysed using the single compartment model and multiple linear regression, giving respiratory resistance ($R_{RS}$), elastance ($E_{RS}$) and compliance ($C_{RS}$). The measurement of $R_{RS}$ reflects both narrowing of the conducting airways and alterations in the lung. The measurement of $C_{RS}$ and $E_{RS}$ reflects only events in the lung periphery, particularly airway closure leading to lung unit de-recruitment. By contrast, a selective change in $C_{RS}$ is indicative of a more distal site of action.

More thorough evaluations of lung mechanics were made using forced oscillation technique (FOT) according to Jonasson et al., *Respir. Res.*, 9, 23 (2008) and *Respir. Physiol. Neurobiol.*, 165, 229 (2009). The parameters obtained from the FOT measurements in this study were: Newtonian resistance ($R_N$), tissue damping (G), which is closely related to tissue resistance and reflects energy dissipation in the lung tissues; and tissue elastance (H), which characterises tissue stiffness and reflects energy storage in the tissues.

Dynamic pressure-volume (PV) curves were determined by inflating the lungs to a maximum pressure of 30 cm $H_2O$, allowing passive exhalation using the computer-controlled Flexivent ventilator for measuring volume and pressure. Individual results from each animal were compiled. All PV-measurements were performed in triplicate. Quasi-static PV loops were obtained by a slow stepwise inflation and deflation of the lungs. PV loops were performed for PEEP-levels, 3 cm $H_2O$. The shape factor (k) of the descending limb of the PV loop was calculated by fitting the data to the Salazar-Knowles equation. The value of the parameter k is believed to change characteristically with both fibrosis and emphysema. The quasi-static compliance (Cst) and elastance (Est) and the volume air inspired sufficient to reach 20 cm water were also obtained.

Bronchoalveolar lavage (BAL) was carried out essentially as described in Example 4 above, as was flow cytometry analysis of cells from BAL and analysis of inflammatory mediators in BAL and serum.

Frozen lung tissue was homogenised together with 1 mL PBS in a 2 mL tube, using a mixer mill (Retch mm400) for 2 minutes at 4° C. Immediately after homogenisation, the tube was centrifuged for 15 minutes (1500 rpm, 4° C.). The supernatant was removed and saved for protein concentration determination using a NanoDrop spectrophotometer (Proteins A280). After analysing the protein content, equal amounts of protein from each sample were saved for the transforming growth factor beta (TGFβ) 1-3 analysis. TGFβ1-3 was analysed simultaneously using a multiplex kit (Bio-Plex Pro TGF-β 3-Plex Immunoassay) in lung tissue homogenate according to the manufacturer's instructions (Bio-Rad) and analysed on a Bio-Plex™ system (Luminex Bio-Plex™ 200 System, Bio-Rad, Hercules, Calif.).

Animals undergoing histological analysis did not undergo respiratory function testing in order to preserve tissue integrity. The right lung lobe was removed and fixed in 4% paraformaldehyde until paraffin embedding. After embedding in paraffin, the tissue was cut into 3 μm thick sections and mounted on positively charged slides. To assess inflammatory cell infiltration, the sections were deparaffinised, dehydrated, and stained with hematoxylin and eosin. Histopathological evaluation of stained sections was performed by a professional pathologist specialized in small animals at the National Veterinary Institute (SVA) in Uppsala, Sweden.

Statistical analysis was carried out essentially as described in Example 4 above.

Results

In Table 1 below, the numbers of mice used for the different analyses are listed. Blood was sampled from all mice.

TABLE 1

|  | Airway physiology, BAL and serum | Histology and serum |
|---|---|---|
| Gr. 1 | 9 | 3 |
| Gr. 2 | 7 | 3 |
| Gr. 3 | 9 | 3 |
| Gr. 4 | 8 | 3 |
| Gr. 5 | 7 | 3 |

During the 90 days exposure, 5 mice died. In most cases they were euthanised due to worsened health status such as large weight decrease and lethargy, see Table 5. During analysis, 6 mice were significant outliers and therefore excluded from the data set (Table 2).

TABLE 2

|  | Excluded due to worsened health status during CS | Excluded from data set (statistically tested) |
|---|---|---|
| Gr. 1 | — | 2 |
| Gr. 2 | 2 | 1 |
| Gr. 3 | — | 3 |
| Gr. 4 | 1 | — |
| Gr. 5 | 2 | — |

All CS-exposed mice were visibly affected by the exposure. They were suffering from ruffled fur and loss of muscle strength. Animals receiving NBMI (Gr. 3 and Gr. 4.) seemed to some extent healthier than the other groups receiving placebo (animal technician's observation). The injection site for s.c. administration of NBMI was altered to avoid scarring and ulceration. Despite this effort, mice in Gr. 5 established wounds and bunions in the neck. The two other NBMI groups showed no signs of ulceration, neither did the placebo groups. Control animals received DMSO in the same concentration as NBMI in Gr. 5.

CS-exposed animals showed a significant weight difference from control animals on Day 90. Control mice increased 15% in body weight (2.8±0.2 g), whereas mice exposed to CS did not increase body weight to a significant degree (−0.1±0.3 g). Animals receiving NBMI had all gained weight compared to start weight (Gr. 3: 1.0±0.4 g, Gr. 4: 0.7±0.2 g and Gr. 5: 0.6±0.2 g).

The total BAL cell count in CS-exposed animals at Day 90 was significantly higher than in control groups (246,700±21,980 cells/mL with CS and 152,000±20,540 cells/mL without CS, p<0.01). CS-exposure induced a significant increase of macrophages in BAL fluid (229,300±21,400 cells/mL with CS, and 134,200±18,600 cells/mL without CS, p<0.01).

CS-exposure did not increase the number of infiltrated neutrophils and lymphocytes in BAL fluid as compared to the control group (Gr. 1). Animals receiving NBMI (30, 60 and 150 mg/kg) did not have significantly lower numbers of macrophages in BAL fluid. However, there was a tendency to a lower number of neutrophils in Gr. 4 and Gr. 5 and a lower number of lymphocytes in the groups treated with NMBI.

Ninety days of CS-exposure did not significantly increase the levels of either T helper (CD4+/CD3+) or T cytotoxic (CD8+/CD3+) lymphocytes in BAL fluid shown by FACS analysis. The percentage of both lymphocyte types was not significant altered after NBMI treatment. However, since the lymphocytes were reduced after NBMI treatment, there was a significant decrease of T cytotoxic (CD8+/CD3+) lymphocytes in BAL fluid in NBMI treated animals as compared to Gr. 2.

Ninety days of CS exposure induced structural changes in the lung compared to control animals (Gr. 2 vs. Gr. 1), as manifest by CS-induced alterations in both larger and smaller airways by increasing $E_{RS}$ and H together with a decreased $C_{RS}$. CS-decreased hysteresivity coefficient η reflected decreased heterogeneities in the lungs.

Higher doses of NBMI (Gr. 4 and Gr. 5) increased smaller and larger airway resistance ($R_{RS}$ and G) significantly.

PV-curves were measured in mice exposed to CS (Gr. 2) and were compared to mice exposed to room air (Gr. 1). CS exposure significantly made the lung stiffer and larger pressure was needed to inflate the lung. Animals receiving NBMI (30, 60 and 150 mg/kg) did not display significantly changed respiratory function as compared to placebo group (Gr. 2). Cst, Est and k were not affected by smoke-exposure.

Ninety days of CS-exposure did not significantly increase the levels of inflammatory mediators in BAL and serum. In the NBMI 150 mg/kg Group (Gr. 5), the levels of MIP-1β ($p<0.05$) and GM-CSF ($p<0.01$) were lowered in serum when compared to the CS-exposed placebo group (Gr. 2). There were no other significant differences between the inflammatory mediators analysed.

CS-exposed animals (Gr. 2) did not show increased levels of TGFβ in lung homogenate as compared to control group (Gr. 1). Animals receiving NBMI did not have significantly changed amount of TGFβ1-3 compared to the placebo group receiving CS (Gr. 2).

Bronchial lumens and alveoli in all lungs showed a few macrophages. In treated groups, macrophages were slightly more numerous and displayed cytoplasmic yellowish pigment or black pigment granules. The black pigment could possibly be soot from the cigarette exposure and the yellowish pigment might be lipofuscin.

Low numbers of leukocytes (neutrophils, eosinophils, monocytes, macrophages) were observed in occasional alveolar septa and also sub-pleurally in peripheral lung areas in CS-exposed animals. The slightly elevated numbers of macrophages in cigarette-exposed groups was subtle and the lungs remained well under the threshold of inflammation. Observed changes were not sufficiently intense to cause clinical signs.

The control animals in this study showed a significantly better airway function and larger weight gain than the CS-exposed mice, but the increase of cellular cells in BAL fluid was not significantly different from Gr. 2. Control mice received the same treatment as Gr. 2 apart from not being exposed to CS-smoke. However, all animals shared the same accommodation in the laboratory.

CONCLUSION

CS-exposed mice showed weight loss (or lack of increased weight), increase of macrophages, and a stiffer lung together with a decrease of respiratory compliance.

Treatment with NBMI (Gr. 3 and Gr. 4) improves the health status in mice exposed to CS daily for 90 days. A positive treatment effect is supported by increased weight, and a tendency towards decreased numbers of lymphocytes, and a decrease of CD8+ cells, in BAL fluid compared to the CS-exposed Placebo Group (Gr. 2).

The invention claimed is:

1. A method of treatment of chronic obstructive pulmonary disease, which method comprises the administration of N,N-bis-2-mercaptoethyl isophthalamide, or a pharmaceutically acceptable salt thereof, to a patient in need of such treatment.

2. A method as claimed in claim 1, wherein the dose of N,N-bis-2-mercaptoethyl isophthalamide or salt thereof that is administered is capable of regenerating ascorbate systemically.

3. A method of reducing the risk of respiratory morbidity and/or mortality in a patient, which method comprises administering N,N-bis-2-mercaptoethyl isophthalamide, or a pharmaceutically acceptable salt thereof, to such a patient exhibiting symptoms of chronic obstructive pulmonary disease.

4. A method of relieving one or more symptom of chronic obstructive pulmonary disease in a patient suffering therefrom, which method comprise administering N,N-bis-2-mercaptoethyl isophthalamide, or a pharmaceutically acceptable salt or thereof, to such a patient.

5. A method as claimed in claim 4, wherein the symptom is skeletal muscle fatigue and/or cough/sputum production.

6. A method as claimed in claim 1, wherein the patient is a smoker or an ex-smoker.

7. A method as claimed in claim 6, wherein the patient is also receiving therapy which comprises administration of an active ingredient selected from a bronchodilator, an anticholinergic drug, or a corticosteroid.

8. A method as claimed in claim 3, wherein the patient is a smoker or an ex-smoker.

9. A method as claimed in claim 8, wherein the patient is also receiving therapy which comprises administration of an active ingredient selected from a bronchodilator, an anticholinergic drug, or a corticosteroid.

10. A method as claimed in claim 4, wherein the patient is a smoker or an ex- smoker.

11. A method as claimed in claim 10, wherein the patient is also receiving therapy which comprises administration of an active ingredient selected from a bronchodilator, an anticholinergic drug, or a corticosteroid.

* * * * *